(12) United States Patent
Song et al.

(10) Patent No.: US 8,283,129 B2
(45) Date of Patent: Oct. 9, 2012

(54) CHARACTERIZATION OF ESM-1 AS A TUMOR ASSOCIATED MARKER OF COLORECTAL CANCER

(75) Inventors: Eun Young Song, Seoul (KR); Mi Young Park, Jeonju-si (KR); Hyang Sin Lee, Daejeon (KR); Hee Gu Lee, Daejeon (KR); Jae Wha Kim, Daejeon (KR); In Seong Choe, Daejeon (KR); Min A Kang, Gumi-si (KR); Mi Sun Won, Daejeon (KR); Kyung-Sook Chung, Daejeon (KR); Young Ho Kim, Seoul (KR); Ho Kyung Chun, Seoul (KR); Young Il Yeom, Daejeon (KR); Seon-Young Kim, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 99 days.

(21) Appl. No.: 12/744,223

(22) PCT Filed: Nov. 23, 2007

(86) PCT No.: PCT/KR2007/005965
§ 371 (c)(1),
(2), (4) Date: May 25, 2010

(87) PCT Pub. No.: WO2009/066821
PCT Pub. Date: May 28, 2009

(65) Prior Publication Data
US 2010/0248244 A1    Sep. 30, 2010

(30) Foreign Application Priority Data

Nov. 22, 2007 (KR) .......................... 10-2007-0119936

(51) Int. Cl.
*G01N 33/574* (2006.01)
(52) U.S. Cl. ..................................................... 435/7.23
(58) Field of Classification Search ........................ None
See application file for complete search history.

(56) References Cited

U.S. PATENT DOCUMENTS

2003/0108926 A1    6/2003    Mack et al.
2004/0167067 A1    8/2004    Griggs et al.

FOREIGN PATENT DOCUMENTS

WO    WO 2004/021978 A2    3/2004
WO    WO 2007/032631 A1    3/2007

OTHER PUBLICATIONS

International Search Report from International Application No. PCT/KR2007/005965, dated Jul. 25, 2008 (date of completion of search) and Jul. 28, 2008 (date of mailing of report).
Ji et al., "Identification of Endothelial Cell-Specific Molecule-1 as a Potential Serum Marker for Colorectal Cancer," Cancer Sci. 101:2248-2253, 2010.
Jin et al., "Serum Cancer Biomarker Discovery Through Analysis of Gene Expression Data Sets Across Multiple Tumor and Normal Tissues," J. Biomed. Informatics 44:1076-1085, 2011.

*Primary Examiner* — Sheela J Huff
(74) *Attorney, Agent, or Firm* — Clark & Elbing LLP (57) ABSTRACT

Disclosed herein is a colorectal cancer marker for diagnosing colorectal cancer based on ESM-I overexpression in tissues, cells or body fluids of colorectal cancer patients. Disclosed also is the use of the colorectal cancer marker in the development of therapeutic agents for cancer and in the diagnosis and treatment of colorectal cancer.

1 Claim, 2 Drawing Sheets

[FIG. 1]

ESM1

T  NT  T  NT  T  NT  T  NT  M  T  NT  T  NT  T  NT  T  NT

*B*-actin

T  NT  T  NT  T  NT  T  NT  M  T  NT  T  NT  T  NT  T  NT

Sample: 1, 53, 151, 153, 175, 188, 207, 235 (T,NT)
Samsung Medical Center cDNA sample ( 0.7ul/tube )

[FIG. 2]

Lane 1, DLD-1; Lane 2, HT29; Lane 3, HCT116; Lane 4, colo205; Lane 5, SW480;
Lane 6, SW620; Lane 7, SNU C1; Lane 8, SNU C2A; Lane 9, km12 C; Lane 10, KM 12SM

[FIG. 3]

CHARACTERIZATION OF ESM-1 AS A TUMOR ASSOCIATED MARKER OF COLORECTAL CANCER

CROSS-REFERENCE TO RELATED APPLICATIONS

This application is the U.S. national stage filing under 35 U.S.C. §371 of international application PCT/KR2007/005965, filed Nov. 23, 2007, which claims the benefit of Korean Patent Application 10-2007-0119936, filed Nov. 22, 2007.

TECHNICAL FIELD

The present invention relates to methods of identifying the clinical importance and biological functions of endothelial cell-specific molecule-1 (ESM-1) in patients having colorectal cancer and of exploring its potential as a diagnostic marker of colorectal cancer.

BACKGROUND ART

Colorectal cancer is common in many Western countries, and this is associated with diets high in animal fat and meat. It is the second most common form of cancer and the second most important cause of cancer-related death. The incidence of colorectal cancer is also rising in Asia, including Korea and Japan, where colorectal cancer was less common than in the Western world, owing to the Westernization of the diet. A recent survey (2002), conducted by the Korean National Statistical Office, showed that colorectal cancer is the fourth most common cause of cancer death in Korea, after cancer of the lung, stomach and liver. Various methods including fecal occult blood test and colonoscopy are currently used for screening colorectal cancer and increase the rates of detection of early-stage cancer. However, there are few biological markers which can be used for prognosis and to determine suitable therapy for colorectal cancer. Since to date no method capable of accurately diagnosing and staging cancer has been found, a colorectal cancer diagnosis is obtained using a variety of screening methods, including doctor's examination, histological examination, cytological examination, endoscopy, tumor marker detection, imaging test and nuclear medical examination. A tumor marker test is used to screen for and diagnose a specific type of cancer by detecting a tumor marker in blood, tissue and urine specimens. However, since many tumor markers are elevated or detected in biological specimens from individuals not afflicted with cancer, a tumor marker test is not reliable enough to detect and diagnose cancer.

Colorectal cancer is typically screened using common traditional procedures, a guaiac-based fecal occult blood test (FOBT) and colonoscopy. With the recent advances in molecular biology, cyclooxygenase 2 and SFRP2 methylation are becoming known as novel markers for screening colorectal cancer. Carcinoembryonic antigen (CEA) is a glycoprotein that was first identified in 1965 and is detected in colon carcinoma and embryonic colonic mucosa. CEA is considered to be a fetal antigen that is normally present in embryonic and fetal digestive tissues between two and six months and disappears after birth. However, it may reappear in adults who develop colorectal carcinoma and several other neoplastic conditions, including gastrointestinal, pancreatic and lung carcinomas. Due to its reappearance in malignant tissues, CEA is deemed valuable as a marker to help diagnose cancer, to monitor patients who have undergone surgery, or to monitor patients' response to treatment. When the serum CEA level is high before surgery in colorectal cancer or stomach cancer, patients are expected to have a high risk of recurrence. Thus, the CEA level seems to be a valuable prognostic indicator. Since the CEA level is increased in colorectal cancer and also in several other types of cancer in the pancreas (60-90%), stomach (40-600), lung (60-75%), breast (20-50%), and the like, it is commonly used as a broad-spectrum tumor marker. In particular, in colorectal cancer, according to the degree of tumor invasion and spread, CEA levels are elevated in 20-40% of tumors limited to the bowel wall and in 80-90% of tumors metastasized to the liver and other organs. When the cancer has metastasized to the liver, CEA levels sharply rise. Thus, CEA levels are monitored to determine the prognosis of patients having colorectal cancer or to follow up on patients after surgery. In addition to in malignant tumors, Elevated CEA levels occur in various benign diseases including liver cirrhosis, alcoholic hepatitis, pancreatitis, and ulcerative colitis. Colorectal cancer can be sometimes associated with known risk factors. These include increasing age and smoking, which is modifiable.

As another tumor marker, carbohydrate antigen 19-9 (CA 19-9) was defined initially by a monoclonal antibody isolated from mice immunized with a human colorectal carcinoma cell line, which expresses an antigen that is strongly positive in pancreatic ductal adenocarcinoma. The CA 19-9 antigen is positive in pancreatic cancer (84%), gastric cancer (35%), liver cancer (22%) and gallbladder cancer (69%), and is elevated to a high concentration of 1,000 U/ml or more in 40-50% of cancer of the pancreas and bile duct. Thus, the CA 19-9 antigen is considered useful for the early diagnosis of cancer and to help diagnose pancreatic cancer. Gastric and colorectal carcinomas are positive for CA 19-9, especially when they have metastasized to the liver. The antigen is also found in normal tissues of the pancreas and in non-cancerous cells surrounding biliary, gastric mucosal and salivary epithelial carcinomas.

Endothelial cell-specific molecule-1 (ESM-1), also called endocan. The ESM-1 secretory protein is constituted of a polypeptide of 184 amino acids corresponding to a molecular mass of about 20 kDa. Endocan is specifically associated with insulin-like growth factor to promote cell growth and proliferation, and its expression is induced by TNF-alpha and IL-1 beta. ESM-1 has been known as a diagnostic marker of sepsis (Reinhart K et al., Crit Care Clin, 2006, 22(3), 503-519, Filep J G. Crit Care Med, 2006, 34(2), 574-575, Scherpereel A et al., 2006, 34(2), 532-537). Endocan has been reported as a VEGF-A and PI3K regulated gene with increased expression in renal cancer (Rennel E et al., Exp Cell Res, 2007, 313(7): 1285-1294). In lung carcinoma, contamination rates of leukaphereses were assessed by determining ESM-1 expression using immunocytochemistry and RT-PCR (L Perey et al., Br. J Cancer, 2001, 85(11):1713-21). However, there is no report disclosing the utility of ESM-1 as a diagnostic marker of colorectal cancer thorough quantitative analysis in sera and tissues. At present, ESM-1 expression levels are analyzed using general molecular biological methods, while circulating levels (protein levels) thereof are detected using Western blotting, ELISA (David B et al., J. Vasc. Res, 2000, 37, 417-425, USP 2004/0063164A1) and immunohistochemistry using antibodies. USP 2004/0063164A1, titled "Kit and Method for Detecting the ESM-1 Protein", discloses a kit for detecting ESM-1. However, the kit is provided not for diagnosing and treating colorectal cancer, as in the present invention, but for detecting in vitro deteriorations of endothelial vascular wall by measuring ESM-1 levels.

The inventors of this application examined the biological functions of ESM-1 in colorectal cancer and evaluated its potential as a diagnostic and prognostic marker of colorectal cancer. cDNA microarray analysis and RT-PCR for ESM-1 RNA levels using tissues from normal subjects and colorectal cancer patients revealed that ESM-1 is more highly expressed in colorectal carcinoma tissues than nontumorous or normal colorectal tissues. Western blot and immunodot assays for serum ESM-1 protein levels using an antibody against ESM-1 showed higher levels of ESM-1 circulating in the serum of colorectal cancer patients compared to in the serum of normal subjects. These results indicated that ESM-1 is highly useful as a marker for the diagnosis and prognosis of colorectal cancer, leading to the present invention.

DISCLOSURE

Technical Problem

It is therefore an object of the present invention to provide a method of diagnosing colorectal cancer using an ESM-1 gene, a fragment thereof, or an antibody against it, and a diagnostic kit for colorectal cancer.

It is another object of the present invention to provide a small interfering RNA (siRNA) molecule for preventing or treating the incidence or metastasis of colorectal cancer, which has a nucleotide sequence complementary to mRNA derived from an ESM-1 gene or a fragment thereof.

It is a further object of the present invention to provide a method of screening a cancer repressor by determining the ability of a candidate compound to promote or inhibit the action of a protein encoded by the above gene.

Technical Solution

In order to identify the clinical importance and biological functions of ESM-1, the potential of ESM-1 as a diagnostic and prognostic marker for colorectal cancer was evaluated by measuring its RNA and protein levels in tissues and blood samples from patients having colorectal cancer. cDNA microarray analysis, RT-PCR and Western blotting using tissues from colorectal cancer patients showed that ESM-1 is more highly expressed as evidenced by both RNA and protein levels in colorectal carcinoma tissues than nontumorous colorectal tissues. Also, RT-PCR using cell lines revealed that the colorectal carcinoma cell lines SW620 SNU-C2A and DLD1 express high levels of ESM-1. The analysis of clinical serum samples for ESM-1 distribution showed that high levels of ESM-1 are secreted in colorectal cancer.

These results indicated that ESM-1 is useful for the early diagnosis, prognosis, treatment and monitoring of colorectal cancer, leading to the present invention.

In one aspect, the present invention relates to a diagnostic marker of colorectal cancer comprising an ESM-1 nucleic acid or protein.

The term "diagnosis", as used herein, refers to the identification of the presence or properties of colorectal cancer conditions. With respect to the objects of the present invention, the diagnosis indicates the identification of the incidence of colorectal cancer by detecting the expression of a diagnostic marker for colorectal cancer.

The term "marker", as used herein, is intended to indicate a substance that is able to diagnose colorectal cancer by distinguishing cancerous cells from normal cells. The marker is a nucleic acid marker for the ESM-1 gene or a polypeptide marker for the ESM-1 protein, and its expression is increased in colorectal carcinoma cells compared to normal cells.

The human colorectal cancer-specific ESM-1 gene according to the present invention has a full-length nucleotide sequence of 1,644 bp, as shown in SEQ ID No. 1, and is translated into a precursor polypeptide of 184 amino acids, corresponding to a molecular mass of about 20 kDa.

Real-time RT-PCR showed that the ESM-1 gene is expressed at higher levels in colorectal carcinoma tissues than in normal (nontumorous) tissues, indicating that the ESM-1 gene is a tumorigenic/metastatic gene causing colorectal cancer. Thus, the colorectal cancer gene of the present invention is deemed to be involved in colorectal oncogenesis, and is useful in the diagnosis of colorectal cancer, generation of transgenic animals, screening of anticancer agents specific to colorectal cancer and siRNA gene therapy, as well as for controlling human life span.

In another aspect, the present invention relates to a composition for diagnosing colorectal cancer comprising an agent detecting expression levels of the ESM-1 gene or protein.

The expression levels of the ESM-1 marker gene in biological samples may be determined by measuring mRNA or protein levels. The mRNA or protein isolation from a biological sample may be carried out using a known process, and may be quantitatively assessed using various analytical methods.

The term "the measurement of mRNA expression levels", as used herein, refers to a process of assessing the presence and expression levels of mRNA of the ESM marker gene in biological samples for detecting the ESM marker gene, in which the amount of mRNA is measured. Analytical methods for detecting mRNA levels include, but are not limited to, RT-PCR, competitive RT-PCR, real-time RT-PCR, RNase protection assay (RPA), Northern blotting, and DNA chip assay. With the detection methods, a patient suspected of having colorectal cancer may be compared with a normal control for mRNA expression levels of the ESM-1 marker gene, and the patient's suspected colorectal cancer may be diagnosed by determining whether expression levels of mRNA from the ESM-1 marker gene have significantly increased.

The term "the measurement of protein expression levels", as used herein, is a process of assessing the presence and expression levels of proteins coded for the ESM-1 marker gene in biological samples, in which the amount of the protein product of the marker gene is measured using an antibody specifically binding to the protein. Analytical methods for measuring the protein level include, but are not limited to, Western blotting, enzyme-linked immunosorbent assay (ELISA), radioimmunoassay (RIA), radioimmunodiffusion, ouchterlony immunodiffusion, rocket immunoelectrophoresis, immunohistostaining, immunoprecipitation assay, complement fixation assay, FACS, and protein chip assay.

Thus, in one detailed aspect, the present invention provides a composition for detecting a diagnostic marker of colorectal cancer comprising primer sequences complementary to mRNA of the ESM-1 gene.

The "primer" refers to a short nucleic acid sequence having a free 3' hydroxyl group, which is able to form base-pairing interaction with a complementary template and serves as a starting point for replicating the template strand. A primer is able to initiate DNA synthesis in the presence of a reagent for polymerization and four different nucleoside triphosphates at suitable buffers and temperature. The primer may have additional properties that do not change the ability of the primer to serve as an origin for DNA synthesis. The primers may be chemically synthesized using a phosphoramidite solid support method or other widely known methods. These nucleic acid sequences may also be modified using any means known in the art.

In the practice of the present invention, the composition for detecting a diagnostic marker of colorectal cancer includes a pair of primers specific to the ESM-1 gene. Primers for amplifying ESM-1 (SEQ ID No. 1) are preferably represented by SEQ ID Nos. 2 and 3.

In a further aspect, the present invention provides a composition for detecting a diagnostic marker of colorectal cancer, comprising an antibody specific to the ESM-1 protein.

The term "antibody", as used herein, refers to a specific protein molecule that indicates an antigenic region. With respect to the objects of the present invention, an "antibody" binds specifically to the ESM-1 marker protein, and includes all of polyclonal antibodies, monoclonal antibodies and recombinant antibodies.

Antibody production using the colorectal cancer marker protein identified as described above may be easily carried out using techniques widely known in the art.

Polyclonal antibodies may be produced using a method widely known in the art, which includes injecting the ESM-1 protein antigen into an animal and collecting blood samples from the animal to obtain sera containing antibodies. Such polyclonal antibodies may be prepared from certain animal hosts, such as goats, rabbits and pigs. Monoclonal antibodies may be prepared by a method widely known in the art, such as a hybridoma method (see Kohler and Milstein (1976) European Journal of Immunology 6:511-519), or a phage antibody library technique (Clackson et al., Nature, 352:624-628, 1991; Marks et al., J. Mol. Biol., 222:58, 1-597, 1991).

The hybridoma method employs cells from an immunologically suitable host animal injected with the ESM-1 protein as an antigen, such as mice, and a carcinoma or myeloma cell line as another group. Cells of the two groups are fused with each other using a method widely known in the art, for example, using polyethylene glycol (PEG), and antibody-producing cells are propagated using a standard tissue culture method. After uniform cell colonies are obtained through subcloning using a limited dilution technique, hybridomas capable of producing an antibody specific for the ESM-1 protein are cultivated in large scale in vitro or in vivo according to a standard technique.

The phage antibody library method includes constructing a phage antibody library in vitro by obtaining genes for antibodies to the ESM-1 protein and expressing them in fusion protein form on the surface of phages, and isolating monoclonal antibodies binding to the ESM-1 protein from the library.

Antibodies prepared using the above methods are isolated and purified using gel electrophoresis, dialysis, ion exchange chromatography, affinity chromatography, and the like.

In addition, the antibodies of the present invention include complete forms having two full-length light chains and two full-length heavy chains, as well as functional fragments of antibody molecules. The functional fragments of antibody molecules refer to fragments retaining at least an antigen-binding function, and include Fab, F(ab'), P(ab')$_2$, F(ab)$_2$ and Fv.

In yet another aspect, the present invention provides a kit for diagnosing colorectal cancer comprising the composition for diagnosing colorectal cancer according to the present invention. Preferably, the kit for diagnosing colorectal cancer further includes a composition, solution or apparatus, which includes one or more kinds of different constituents suitable for analytical methods.

In one detailed aspect, the diagnostic kit may be featured by comprising essential elements required for performing RT-PCR. An RT-PCR kit includes a pair of primers specific for each marker gene. The primer is a nucleotide having a sequence specific to a nucleic acid sequence of each marker gene, and is about 7 bp to 50 bp in length, more preferably about 10 bp to 30 bp in length. Also, the RT-PCR kit may include primers specific to a nucleic acid sequence of a control gene. The RT-PCR kit may further include test tubes or other suitable containers, reaction buffers (varying in pH and magnesium concentrations), deoxynucleotides (dNTPs), enzymes such as Taq-polymerase and reverse transcriptase, DNAse, RNAse inhibitor, DEPC-treated water, and sterile water.

In another detailed aspect, the diagnostic kit may be featured by comprising essential elements required for performing a DNA chip assay. A DNA chip kit may include a base plate, onto which genes or fragments thereof, cDNA, or oligonucleotides are attached, and reagents, agents and enzymes for preparing fluorescent probes. Also, the base plate may include cDNA or oligonucleotides corresponding to a control gene or fragments thereof.

In a further detailed aspect, the diagnostic kit may be featured by comprising an antibody specifically binding to the ESM-1 protein. The diagnostic kit is preferably an ELISA kit. The ELISA kit may also include an antibody specific to a control protein. The ELISA kit may further include reagents capable of detecting bound antibodies, for example, a labeled secondary antibody, chromophores, enzymes conjugated with an antibody and their substrates, or other substances capable of binding to the antibodies.

In still another aspect, the present invention provides a method of diagnosing colorectal cancer using the composition for diagnosing colorectal cancer or the kit for diagnosing colorectal cancer.

In one detailed aspect, the present invention provides a method of diagnosing colorectal cancer comprising measuring mRNA levels of the ESM-1 gene in a biological sample from a patient suspected of having colorectal cancer using primers specific to the ESM-1 gene; and comparing mRNA levels of the sample from the patient with those of a normal control sample to determine the increase in mRNA levels.

The term "biological sample", as used herein, refers to tissues, cells and others, in which a difference in mRNA or protein expression levels of the ESM-1 marker gene can be detected. Examples of the biological samples include, but are not limited to, urine, whole blood, plasma and sera.

Analytical methods for measuring mRNA levels include, but are not limited to, RT-PCR, competitive RT-PCR, real-time RT-PCR, RNase protection assay (RPA), Northern blotting, and DNA chip assay.

With the detection methods, a patient suspected of having colorectal cancer may be compared with a normal control for mRNA expression levels of the ESM-1 gene, and the patient's suspected colorectal cancer may be diagnosed by determining whether expression levels of mRNA from the colorectal cancer marker gene have significantly increased.

The measurement of mRNA expression levels is preferably carried out using RT-PCR with primers specific to a gene used as a colorectal cancer marker, or using a DNA chip.

Figure 1:
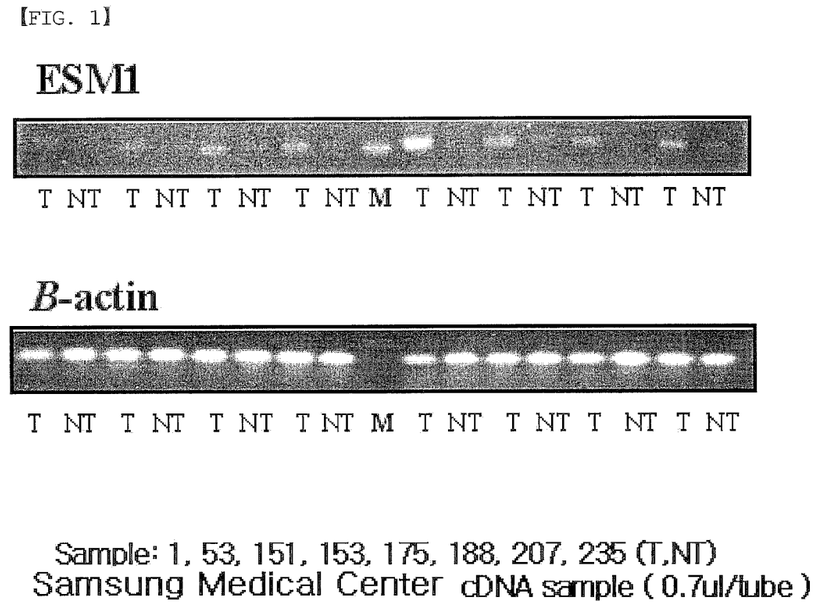
FIG. 1 shows the results of RT-PCR for ESM-1 expression in tumorous (T) and nontumorous (NT) tissues from colorectal cancer patients.
Figure 2:
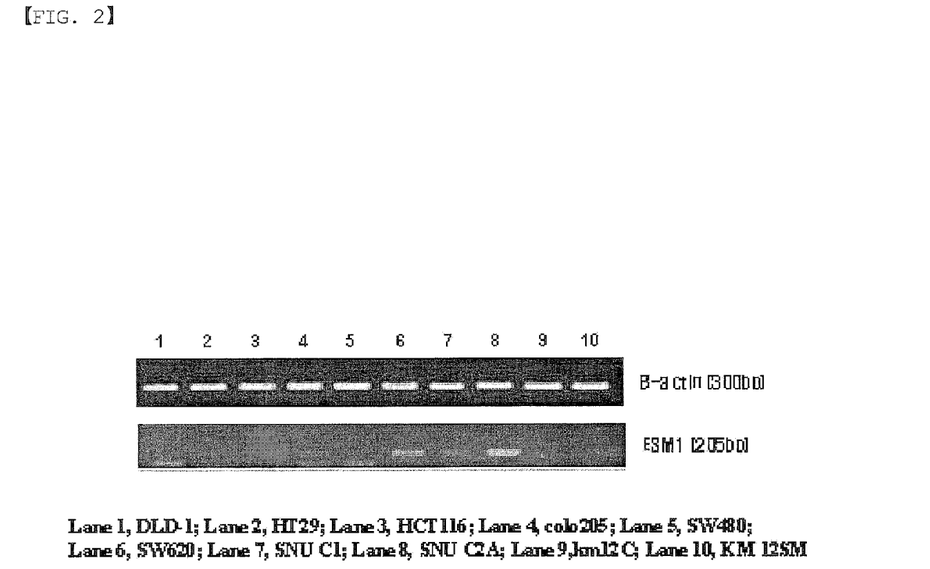
FIG. 2 shows ESM-1 expression levels in colorectal carcinoma cell lines.

RT-PCR is a method capable of simply diagnosing the incidence of colorectal cancer by electrophoresing RT-PCR products and analyzing patterns and thicknesses of bands in order to determine the expression and levels of mRNA from a gene used as a diagnostic marker of colorectal cancer while comparing the mRNA expression and levels with those of a control (FIGS. 1 and 2). Alternatively, the measurement of mRNA expression levels is carried out using a DNA chip in which the colorectal cancer marker gene or nucleic acid fragments thereof are anchored at high density to a glass-like base plate. A cDNA probe labeled with a fluorescent substance either at its end or in the interior thereof is prepared using mRNA isolated from a sample, and is hybridized with the DNA chip. The DNA chip is then read to determine the presence or expression levels of the gene, thereby diagnosing the incidence of colorectal cancer.

In another detailed aspect, the present invention provides a method of diagnosing colorectal cancer comprising detecting protein levels by contacting an antibody specific to the ESM-1 protein with a biological sample from a patient suspected of having colorectal cancer to form antigen-antibody complexes, and comparing protein levels of the sample from the patient with those of a normal control sample to determine an increase in the amount of formed antigen-antibody complexes.

The isolation of proteins from a biological sample may be achieved using a known process, and protein levels may be measured by a variety of methods.

Analytical methods for measuring protein levels include, but are not limited to, ELISA, radioimmunoassay (RIA), sandwich assay, and Western blot or immunoblot assay on a polyacrylamide gel. The methods enable the detection of expression of the above protein in fluid samples from subjects.

With the analytical methods, a patient suspected of having colorectal cancer is compared with a normal control with respect to the amount of formed antigen-antibody complexes, and the patient's suspected colorectal cancer is diagnosed if a significant increase in expression levels of the ESM-1 protein is observed.

The term "antigen-antibody complexes", as used herein, refers to binding products of the ESM-1 protein to an antibody specific thereto. The amount of formed antigen-antibody complexes may be quantitatively determined by measuring the signal size of a detection label. Such a detection label may be selected from the group consisting of enzymes, fluorescent substances, ligands, luminescent substances, microparticles, redox molecules and radioactive isotopes, but the present invention is not limited thereto. Examples of enzymes available as detection labels include, but are not limited to, β-glucuronidase, β-D-glucosidase, β-D-galactosidase, urease, peroxidase or alkaline phosphatase, acetylcholinesterase, glucose oxidase, and hexokinase. Examples of the fluorescent substances include, but are not limited to, fluorescein, phycocyanin, and fluorescamine. Examples of the ligands include, but are not limited to, biotin derivatives. Examples of luminescent substances include, but are not limited to, luciferin. Examples of the microparticles include, but are not limited to, colloidal gold. Examples of the redox molecules include, but are not limited to, quinone, 1,4-benzoquinone, and hydroquinone. Examples of the radioactive isotopes include, but are not limited to, $^3$H and $^{14}$C.

Preferably, the protein expression levels are measured using ELISA. Examples of ELISA include, but are not limited to, direct sandwich ELISA using a labeled antibody recognizing an antigen bound to an antibody immobilized on a solid support; and indirect sandwich ELISA, in which a captured antigen bound to an antibody immobilized on a solid support is detected by first adding an antigen-specific antibody, and then a secondary labeled antibody which binds the antigen-specific antibody. More preferably, the protein expression levels are detected using sandwich ELISA, where a sample reacts with an antibody immobilized on a solid support, and the resulting antigen-antibody complexes are detected by adding a labeled antibody specific for the antigen, followed by enzymatic development, or by adding first an antigen-specific antibody and then a secondary labeled antibody which binds to the antigen-specific antibody, followed by enzymatic development. The incidence of colorectal cancer may be diagnosed by measuring the degree to which the ESM-1 marker protein and an antibody thereto form complexes.

In addition, the measurement of the protein expression levels is preferably carried out using a protein chip in which one or more antibodies to the ESM-1 marker are arrayed and immobilized at predetermined positions of a base plate at high density. Using a method of analyzing a sample using a protein chip, proteins are isolated from the sample and hybridized with the protein chip to form antigen-antibody complexes. The protein chip is then read to determine the presence or expression levels of the proteins, thereby diagnosing the incidence of colorectal cancer.

Figure 3:
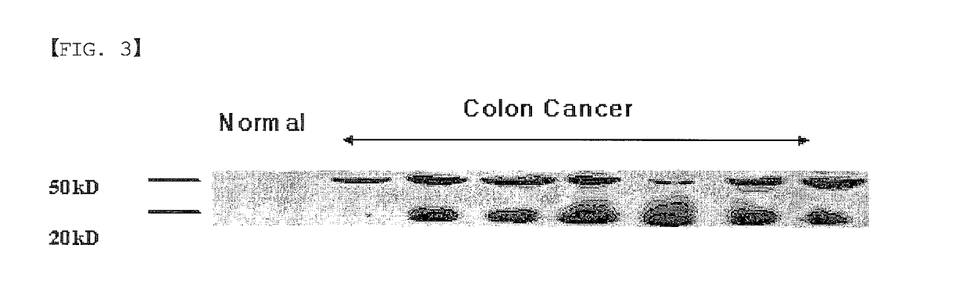
FIG. 3 shows the results of Western blotting for ESM-1 expression in serum samples from colorectal cancer patients.

Further, the measurement of protein expression levels is achieved using Western blotting using an antibody to the ESM-1 protein. Total proteins are isolated from a sample, electrophoresed to separate them according to size, transferred onto a nitrocellulose membrane, and reacted with an antibody. The amount of antigen-antibody complexes produced is detected using a labeled antibody, thereby diagnosing the incidence of colorectal cancer (FIG. 3).

The detection methods comprise comparing the expression level of a maker gene in cells in which colorectal cancer develops with that in a normal control. mRNA or protein levels may be expressed as an absolute or relative difference in the amount of the ESM-1 marker protein.

In still another aspect, the present invention provides a composition for treating or preventing colorectal cancer or inhibiting the metastasis of the cancer comprising a substance suppressing the expression of ESM-1 gene. The composition preferably includes an antisense gene or small interfering RNA (siRNA) against the ESM-1 gene as a substance suppressing ESM-1 gene expression. As used herein, the term "antisense gene" refers to a polynucleotide that has a sequence complementary to a partial or full-length sequence of mRNA transcribed from the ESM-1 gene of SEQ ID No. 1 or a fragment thereof. A specific type of cancer developed by the expression of an oncogene can be treated by introducing a DNA sequence, capable of binding to mRNA from the oncogene and suppressing its translation by ribosome, into a patient. Also, siRNA molecules to the ESM-1 gene are short double-stranded RNA (dsRNA) fragments of about to 30 nucleotides. The endonuclease Dicer recognizes double-stranded RNA and chops it up into small fragments (called small interfering RNA (siRNA)). When introduced into cells, a double-stranded siRNA against the ESM-1 gene interacts with the target mRNA and directs its cleavage via RNA interference, resulting in inhibiting ESM-1 gene expression. The composition according to the present invention is administered into a patient using a common method in order to suppress the expression of a tumorigenic and/or metastatic gene. For example, Filleur et al. reported positive results on the silencing of gene expression by administering siRNAs through low-volume intravenous injection without the use of any facilitated delivery system (Filleur et al., Cancer Res., 63(14):3919-22, 2003). As a strategy to enhance the in vivo absorption and stability of siRNAs, Chien et al. described the use of a liposome to deliver siRNAs through intravenous injection. Delivery efficiency was estimated to be approximately seven times better than with traditional liposomes, and toxicity was lower (Chien et al., Cancer Gene Ther., 12(3): 321-8, 2005).

In addition to one or more effective ingredients selected from the antisense gene and siRNA against ESM-1 gene, the pharmaceutical composition of the present invention may include at least one pharmaceutically acceptable carrier. Examples of the pharmaceutically acceptable carrier include saline solution, sterile water, Ringer's solution, buffered saline solution, dextrose solution, maltodextrin solution, glycerol, ethanol, liposome, and a mixture of two or more thereof. If necessary, the composition may further include other conventional additives, such as antioxidants and buffers. Also, the composition may additionally include diluents, dispersants, surfactants, binders and lubricants in order to be formulated into injection formulations, such as aqueous solution, suspension and emulsion, and into pills, capsules, granules or tablets. The carrier may be used in the form of being coupled to a target-specific antibody or other ligands in order for the effective ingredient to act in a target-specific manner. Furthermore, the composition may be preferably formulated depending on its components, using a suitable method known in the art, for example, the method described in Remington's Pharmaceutical Science (the latest edition), Mack Publishing Company, Easton Pa.

The administration route for the pharmaceutical composition of the present invention is not particularly restricted, but, according to the intended use, the composition may be administered orally or via parenteral routes, for example, intravenous, subcutaneous, intraperitoneal or topical. The specific therapeutically effective dose level for any particular patient may vary depending on a variety of factors, including the patient's weight, age, gender, general health status and diet, the time of administration, route of administration, rate of excretion of the composition, and severity of the illness. The composition may be administered in a daily dosage ranging from about 0.1 to 100 mg/kg, and preferably 0.5 to 10 mg/kg. The daily dosage can be given in a single dose or in several divided doses for preference.

The present invention is not limited to particular formulations, but the pharmaceutical composition is preferably formulated into an injection preparation.

In addition, the present invention enables the establishment of a continuously culturable cell line harboring a reporter system using a promoter of the ESM-1 oncogene. Such a cell line may be useful in anticancer drug screening through the screening of small molecules.

Advantageous Effects

The present invention is characterized by identifying the nature of the ESM-1 protein and utilizing the protein in the diagnosis and treatment of colorectal cancer. In accordance with the present invention, the ESM-1 secretory protein is more highly expressed in colorectal cancer patients than in normal individuals. Such cancer-specific high expression of ESM-1 is useful in the diagnosis and treatment of colorectal cancer, as well as in studies for the role of ESM-1 in oncogenesis. Thus, ESM-1 has potential as diagnostic and prognostic agents for colorectal cancer.

MODE FOR INVENTION

A better understanding of the present invention may be obtained through the following examples, which are set forth to illustrate, but are not to be construed as the limit of the present invention.

Example 1

Preparation of Tissue Samples

For a cDNA microarray assay, tumorous and normal nontumorous tissue samples from twenty colorectal cancer patients were obtained from the Samsung Medical Center, Korea, and frozen in liquid nitrogen. Total RNA was isolated using an RNeasy mini kit (Qiagen, Hilden, Germany).

Example 2

Analysis of ESM-1 Expression in Colorectal Carcinoma Tissues 2-1. Analysis of ESM-1 Expression Using DNA Microarray Assay A cDNA microarray assay was performed to find colorectal cancer-associated genes. ESM-1 gene expression was assessed for twenty colorectal carcinoma tissues and normal tissues. As shown in Table 1, below, a significant increase in ESM-1 gene expression was seen in colorectal carcinoma tissues.

TABLE 1

| Target ID | mean | t_test | T1 | T2 | T3 | T4 | TT5 | T6 | T7 | T8 | T9 |
|---|---|---|---|---|---|---|---|---|---|---|---|
| ESM1 | 5.701 | 0.022 | 8.38 | 7.27 | 6.89 | 5.76 | 5.12 | 4.99 | 6.31 | 3.87 | 7.54 |

| Target ID | T10 | T11 | T12 | T13 | T14 | T15 | T16 | T17 | T18 | FC = n |
|---|---|---|---|---|---|---|---|---|---|---|
| ESM1 | 5.33 | 4.76 | 6.46 | 6.64 | 3.78 | 5.96 | 4.33 | 3.14 | 6.09 | 18 |

2-2. Analysis of ESM-1 Expression using RT-PCR

One dozen pairs of tumorous (T) and nontumorous (NT) tissue samples were prepared and assessed for RNA levels using RT-PCR. In brief, oligonucleotides corresponding to the ESM-1 software (http://frodo.wi.mit.edu/). RT-PCR was carried out using first strand cDNA mixture (5 µg RNA) as a template.

Primers for RT-PCR were as follows.

| start . . . end | Direction | Annealing | Primer sequence (205 bp) |
|---|---|---|---|
| (A) 66 . . . 83 | Forward primer | (18/18) | atgaagagcgtcttgctg (SEQ ID No. 2) |
| (B) 253 . . . 270 | Reverse primer | (18/18) | ctgtgcggtagcaagttt (SEQ ID No. 3) |

Primer annealing was carried out at 47.5° C.

ESM-1 mRNA expression was normalized against β-actin as an internal control.

Consistent with the results of the cDNA microarray assay in Example 2-1, ESM-1 mRNA expression was remarkably increased in colorectal carcinoma tissues compared to normal tissues (FIG. 1).

Example 3

Evaluation of ESM-1 Expression in Colorectal Carcinoma Cell Lines and Patient's Sera Western blotting was carried out using a polyclonal antibody against ESM-1 in order to compare ESM-1 protein expression levels between colorectal carcinoma cell lines. Colorectal carcinoma cells were cultured and harvested. The cells were then lysed with a lysis buffer (1% Triton X-100, 150 mM NaCl, 100 mM KCl, 20 mM HEPES (pH 7.9), 10 mM EDTA, 1 mM sodium orthovanadate, 10 µg/ml aprotinin, 10 µg/ml leupeptin, 1 M PMSF). The cell lysates were electrophoresed to be separated according to size, and transferred onto a nitrocellulose membrane (Bio-Rad, CA, USA). The blot was blocked in 5% non-fat dry milk plus 0.1% Tween 20 in PBS for 2 hrs at room temperature. The blocked blot was incubated in an antibody against ESM-1 (1:5,000 diluted) for 2 hrs, and then in a horseradish peroxidase (HRP)-conjugated secondary antibody (1:5,000 diluted) for 1 hr. The blot was then developed using an enhanced chemiluminescence assay kit (Pierce, Ill., USA). As shown in FIG. 2, colorectal carcinoma cell lines, particularly SW620 and SNU-C2A cells, were found to express ESM-1 at high levels. These results indicated that the ESM-1 protein is expressed in colorectal cancer. In addition, Western blotting using serum samples from colorectal cancer patients showed that the ESM-1 protein is present in the sera of colorectal cancer patients (FIG. 3).

Example 4

Evaluation of ESM-1 Protein Expression in the Patient's Sera Using Immunodot Assay The levels of ESM-1 secreted into sera were assessed using an immunodot assay, which was performed using a polyclonal antibody against ESM-1. 2 µl of each of the serum samples (ten per patient), diluted five- and ten-fold, was dotted on a nitrocellulose membrane, and was air-dried at room temperature. The membrane was then blocked in 1% BSAT (bovine serum albumin in Tris-buffered saline). The blocked membrane was incubated in a polyclonal antibody against ESM-1 (1:1,000 diluted), and then in an HRP-conjugated secondary antibody (1:2,000 diluted). The membrane was then developed using a DAB solution (0.5 mg/ml of diaminobenzidine in PBT), and scanned to compare band intensity. More of the ESM-1 protein was found to be secreted into sera in colorectal cancer than into normal sera. These results indicate that ESM-1 has potential as a diagnostic and prognostic marker for colorectal cancer.

Example 5

Preparation of Sandwich ELISA Kit

A sandwich ELISA kit for detecting concentration of ESM-1 was prepared using the following constituents.

A. Capture antibody: an antibody-immobilized microtiter plate was prepared by adding 100 µl of a polyclonal antibody against ESM-1 to a microtiter plate, allowing the antibody to attach to the surface of the plate at 4° C. overnight, and blocking the antibody-bound surface with albumin.

B. Detection antibody: monoclonal antibody against ESM-1

C. Enzyme-conjugated antibody: horseradish peroxidase-conjugated secondary antibody (anti-mouse IgG conjugated with HRP)

D. Serum dilution solution

E. Substrate solution

F. Washing solution: 0.05% Tween in PBS

G. Standard solution: ESM-1 standard solution

Serum samples from colorectal cancer patients can be analyzed to detect ESM-1 levels using the prepared sandwich ELISA kit as follows. Each serum sample is suitably diluted with the serum dilution solution (D). 100 µl of each dilution is added to wells of the microtiter plate to which the capture antibody is attached. Then, ESM-1 levels are assessed using the other constituents B, C and E according to a sandwich ELISA procedure.

The invention claimed is:
1. A method of diagnosing colorectal cancer, comprising:
(a) contacting an antibody specific to an ESM-1 protein with a whole blood, plasma, or serum sample from a patient suspected of having colorectal cancer to form antigen-antibody complexes; and
(b) comparing protein levels of the sample from the patient with those of a normal control sample to determine an increase in the amount of formed antigen-antibody complexes, wherein the increased amount of the antigen-antibody complexes in the sample from the patient as compared to the antigen-antibody complexes in the normal control sample indicates that the patient has a colorectal cancer.

* * * * *

SEQUENCE LISTING

<160> NUMBER OF SEQ ID NOS: 3

<210> SEQ ID NO 1
<211> LENGTH: 183
<212> TYPE: PRT
<213> ORGANISM: Artificial Sequence
<220> FEATURE:
<223> OTHER INFORMATION: Endothelial cell-specific molecule 1 precursor

<400> SEQUENCE: 1

```
Met Lys Ser Val Leu Leu Leu Thr Thr Leu Leu Val Pro Ala His Leu
 1               5                  10                  15

Val Ala Ala Trp Ser Asn Asn Tyr Ala Val Asp Cys Pro Gln His Cys
            20                  25                  30

Asp Ser Glu Cys Lys Ser Ser Pro Arg Cys Lys Arg Thr Val Leu
        35                  40                  45

Asp Asp Cys Gly Cys Cys Arg Val Cys Ala Ala Gly Arg Gly Glu Thr
    50                  55                  60

Cys Tyr Arg Thr Val Ser Gly Met Asp Gly Met Lys Cys Gly Pro Gly
65                  70                  75                  80

Leu Arg Cys Gln Pro Ser Asn Gly Glu Asp Pro Phe Gly Glu Glu Phe
                85                  90                  95

Gly Ile Cys Lys Asp Cys Pro Tyr Gly Thr Phe Gly Met Asp Cys Arg
            100                 105                 110

Glu Thr Cys Asn Cys Gln Ser Gly Ile Cys Asp Arg Gly Thr Gly Lys
        115                 120                 125

Cys Leu Lys Phe Pro Phe Phe Gln Tyr Ser Val Thr Lys Ser Ser Asn
    130                 135                 140

Arg Phe Val Ser Leu Thr His Asp Met Ala Ser Gly Asp Gly Asn Ile
145                 150                 155                 160

Val Arg Glu Glu Val Val Lys Glu Asn Ala Ala Gly Ser Pro Val Met
                165                 170                 175

Arg Lys Trp Leu Asn Pro Arg
            180
```

<210> SEQ ID NO 2
<211> LENGTH: 18
<212> TYPE: DNA
<213> ORGANISM: Artificial Sequence
<220> FEATURE:
<223> OTHER INFORMATION: foward primer for ESM-1

<400> SEQUENCE: 2
atgaagagcg tcttgctg                                                   18

<210> SEQ ID NO 3
<211> LENGTH: 18
<212> TYPE: DNA
<213> ORGANISM: Artificial Sequence
<220> FEATURE:
<223> OTHER INFORMATION: reverse primer for ESM-1

<400> SEQUENCE: 3
ctgtgcggta gcaagttt                                                   18